US005750493A

United States Patent [19]
Sommadossi et al.

[11] Patent Number: 5,750,493
[45] Date of Patent: May 12, 1998

[54] METHOD TO IMPROVE THE BIOLOGICAL AND ANTIVIRAL ACTIVITY OF PROTEASE INHIBITORS

[75] Inventors: Jean-Pierre Sommadossi, Birmingham, Ala.; Raymond F. Schinazi, 1524 Regency Walk Dr., Decatur, Ga. 30033

[73] Assignees: Raymond F. Schinazi, Decatur, Ga.; University of Alabama at Birmingham, Birmingham, Ala.

[21] Appl. No.: 521,474

[22] Filed: Aug. 30, 1995

[51] Int. Cl.$^6$ ............................................. A61K 38/55
[52] U.S. Cl. ........................... 514/1; 514/2; 514/29
[58] Field of Search .................................. 514/1, 2, 29

[56] References Cited

PUBLICATIONS

Copy of written opinion in corresponding PCT Application No. PCT/US96/13721.
Bilello et al, "Reduction of the In Vitro Activity of A77003, an Inhibitor of Human Immunodeficiency Virus Protease, by Human Serum $\alpha_1$ Acid Glycoprotein", The Journal of Infectious Diseases 1995: 171:546–551.
Dette et al, "The Binding Protein of Erythromycin in Human Serum", Biochemical Pharmacology, vol. 35, No. 6, pp. 959–966.
Kageyama et al, "Protein Binding of Human Immunodeficiency Virus Protease KNI-272 and Alteration of Its In Vitro Antiretroviral Activity in the Presence of High Concentrations of Proteins", Antimicrobial Agents and Chemotherapy, May 1994, pp. 1107–1111.
Chatterjee et al, "Reversal of Multidrug Resistance by Verapamil and Modulation by $\alpha_1$–Acid Glycoprotein in Wild–type and Multidrug–resistant Chinese Hamster Ovary Cell Lines", Cancer Research 50, 2818–2822, May 1, 1990 and attached Abstract.
Chatterjee et al, "Reversal of Acquired Resistance to Adriamycin in CHO Cells By Tamoxifen and 4–Hydroxy Tamoxifen: Role of Drug Interaction of Alpha 1 acid Glycoprotein", Br J Cancer, Nov. 1990, 62(5), 712–717 and Attached Abstract.
Urien et al, "ph–Dependency of Basic Ligand Binding to $\alpha_1$–Acid Glycoprotein (Orosomucoid)", Biochem. J., (1991) 280, 277–280 and attached Abstract.
Chatterjee et al, "Enhancement of Adriamycin Cytotoxicity in a Multidrug Resistant Chinese Hamster Ovary (CHO) Ssubline, CHO–Adrr, By Toremifene and Its Modulation of Alpha 1 Acid Glycoprotein", Eur J. Cancer, Apr. 1990, 26(4) 432–436 and attached Abstract.
Abstract: Barre et al., "Pharmacokinetics of erythromycin In Patients With Severe Cirrhosis", Br J. Clin Pharmacol. Jun. 1987, 23(6), pp. 753–757.
Abstract: Qin et al., "Decreased Elimination of Drug in the presence of Alpha–1–Acid Glcyprotein is Related to a Reduced Hepatocyte Uptake", J Pharmcol Exp Ther, Jun. 1994, 269(3), PP. 1176–1181.

Abstract; Heikinheimo et al, "Dose–Responce Relationships of RU 486", Ann Med, Feb. 1993, 25(1), pp. 71–76.
Abstract: Maruyama et al, "Characterization of Drug Binding Sites on Alpha 1–Acid Glcyprotein", Chem Pharm Bull, Jun. 1990, 38(6), pp. 1688–1691.
Abstract: Prandota et al, "Binding of Erythromycin Base to Human Plasma Proteins", J Int Med Res, 1980, 8 Suppl 2, pp. 1–8.
Wanwimolruk et al, "Plasma Protein Binding of Quinine: Binding to Human Serum Albumin, Alpha 1–Acid", J Pharm Pharmacol, Oct. 1992, 44(10) pp. 806–811 and attached Abstract.
Periti et al, "Pharmacokinetic Drug Interactions of Macrolides", m Clin. Pharmacokinet. 23(2)l 106–131, 1992.
Rodvold et al, "New Oral Macrolide and Fluoroquinolone Antibiotics: An Overview of Pharmacokinetics, Interactions, and Safety", Chemotherapy, Clinical Infectious Diseases 1993: 17(Suppl 1):S192–9.
Periti et al, "Clinical Pharmacokinetic Properties of the Macrolide Antibiotics (Part I)", Clinical Pharmacokentics 16: 193–214 (1989).
Periti et al, "Clinical Pharmacokinetic Properties of the Macrolide Antibiotics (Part II)", Clinical Pharmacokinetics 16: 261–282 (1989).
Kremer et al, "Drug Binding to Human Alpha–1–Acid Glcyprotein In Health and Disease", Pharmacological Reviews, (1988), vol. 40, No. 1, pp. 1–47.
"Drug Binding to Alpha 1 Acid Glcyprotei –Clinically Important?" (editorial), Lancet, Feb. 18, 1979, 1(8112), p. 368 and attached Abstract.
Chiang et al, Phamacological Activity of Prazosin is decreased by Alpha–1–Acid Glcyprotein in Vivo, J. Pharmacol Exp Ther, Jul. 1990, 254(1), pp. 324–349 and attached Abstract.
Chang "Progress and Prospects in Protease Inhibitor Research", Journal of the Physicians Assn for AIDS Care, Jul. 1994, pp. 8–15.
Condra et al, "In Vivo Emergence of HIV–1 Variants Resistant to Multiple Protease Inhibitors", Nature, vol. 374, Apr. 6, 1995, pp. 569–571.
McKerrow et al, "The Protease and Pathogenicity of Parasitic Protozoa[1]", Annu. Rev. Microbiol., 1993, 47:821–53.
Richman, "Protease Unhibited", New and Views, Nature, vol. 374, Apr. 5, 1995.

Primary Examiner—James Ketter
Assistant Examiner—John S. Brusca
Attorney, Agent, or Firm—Oblon, Spivak, McClelland, Maier & Neustadt, P.C.

[57] ABSTRACT

Methods for improving the cellular uptake of protease inhibitors (e.g., HIV protease inhibitor), alone or in the presence of one or more additional therapeutic agents, in protease inhibitor-based therapies, involving administration of one or more AAG-binding compounds, such as macrolide or lincosamide antibiotics, which have sufficient binding affinity for AAG to competitively bind AAG in the presence of the protease inhibitor.

39 Claims, No Drawings

METHOD TO IMPROVE THE BIOLOGICAL AND ANTIVIRAL ACTIVITY OF PROTEASE INHIBITORS

BACKGROUND OF THE INVENTION

1. Field of the Invention

The present invention relates to a method for improving cellular uptake of therapeutic agents, such as protease inhibitors and thus increase their activity, especially their anti-HIV activity.

2. Discussion of the Background

The disease now known as AIDS was first recognized as early as 1979. The number of cases reported to the Centers for Disease Control and Prevention (CDC) increased dramatically each year since then, and in 1982 the CDC declared AIDS a new epidemic. Between December 1987 and November 1988, over 32,000 new cases of AIDS were reported by the CDC (HIV/AIDS Surveillance Report, 1–16, Dec. 1989). Over 3,000 new cases were reported in 1984 alone. By early 1995, the World Health Organization (WHO) estimates that at least 4 million cases of the disease have occurred worldwide. It has also been estimated that approximately 10 million people are infected today with HIV.

In the United States, about 441,000 cases of AIDS have been reported to the CDC to date. As of January, 1995, the CDC reported that there have been 250,000 deaths due to AIDS in the United States alone. It is clear that the cost of the AIDS epidemic in terms of human lives is staggering, and the worst is yet to come.

Retroviruses were proposed as the causative agent of AIDS. Recently, human immunodeficiency virus type 1 (HIV) has emerged as a preferred name for the virus responsible for AIDS. Antibodies to HIV are present in over 80% of patients diagnosed as having AIDS or pre-AIDS syndrome, and it has also been found with high frequency in identified risk groups.

There is considerable difficulty in diagnosing the risk of development of AIDS. AIDS is known to eventually develop in almost all of the individuals infected with HIV.

A patient is generally diagnosed as having AIDS when a previously healthy adult with an intact immune system acquires impaired T-cell immunity. The impaired immunity usually appears over a period of 18 months to 3 years. As a result of this impaired immunity, the patient becomes susceptible to opportunistic infections, various types of cancers such as Kaposi's sarcoma, and other disorders associated with reduced functioning of the immune system.

No treatment capable of preventing the disease or significantly reversing the immunodeficiency of AIDS is currently available. All patients with opportunistic infections and approximately half of all patients with Kaposi's sarcoma have died within two years of diagnosis. Attempts at reviving the immune system in patients with AIDS have so far been unsuccessful.

While 3'-azido-3'-deoxythymidine (AZT) has been most often used in treating HIV infection and AIDS, it has considerable negative side effects such as reversible bone marrow toxicity, and the development of viral resistance to AZT by the patient. Thus other methods of treatment are highly desirable.

Viruses traditionally do not respond to antibiotic therapy. Therefore, other treatments are used when treating viral infections. One such recently discovered therapy revolves around the use of protease inhibitors to disrupt the viral replication cycle. Protease inhibitor therapy has the potential to be used in the treatment of a wide range of diseases, including viral infections, such as those caused by retroviruses (e.g., HIV), hepadnaviruses (e.g., hepatitis C virus), herpesviruses (e.g., herpes simplex virus and cytomegalovirus) and myxoviruses (e.g., influenza virus), as well as parasitic protozoa (e.g., cryptosporidium and malaria), in cancer chemotherapy and various pathological disorders. By way of example, the role of HIV protease on the HIV replication cycle is discussed below.

HIV Protease and the Replication Cycle

HIV replicates through a DNA intermediate. Each virus particle contains two identical, single-stranded RNA molecules surrounded by the viral nucleocapsid protein. The remaining core of the virus is composed of the capsid and matrix proteins. Enzymes required for replication and integration of the viral genetic materials into the host cells are also contained within the capsid. The outer coat of the virus particle consists of viral envelope glycoproteins and membrane derived from the host cell.

As with other retroviruses, HIV has the same basic genetic makeup for the gag, pol, and env genes. The gag and pol genes encode the viral capsid proteins and replication enzymes, respectively. These genes are expressed from one intermediate form of viral genetic material, called unspliced messenger RNA, resulting in the synthesis of precursor gag-pol fusion polyprotein. The polyprotein is then cleaved by the HIV protease enzyme to yield the mature viral proteins. The gag precursor is cleaved into p17 (matrix), p24 (capsid), p7 (nucleocapsid), and p6. On the other hand, the pol precursor is processed into individual protease, reverse transcriptase, and integrase enzymes. Thus, HIV protease is responsible for regulating a cascade of cleavage events that lead to the virus particle's maturing into a virus that is capable of full infectivity.

HIV protease is a member of the aspartic protease family. It differs from the mammalian aspartic proteases in that it functions as a homodimer of two subunits. By contrast, the mammalian proteases are monomeric polyproteins. However, the two types of proteases are similar in their overall structure and function. In 1988, it was observed that mutation or deletion of the HIV protease gene results in the production of noninfectious, immature virus particles, suggesting that HIV protease provides an essential function in the replication cycle of HIV and makes the protease an attractive target for the design of specific antiviral drugs for AIDS. The vast body of knowledge accumulated from studies with other aspartic proteases, most notably human renin, has facilitated the design and discovery of HIV protease inhibitors. Recent advances in computer-aided rational drug design have been widely translated in the pharmaceutical and biotechnology industries for the development of potent and highly specific inhibitors of HIV. Protease inhibitors can be rationally improved in their in vitro activity, if the architecture of the protease-inhibitor complex is determined by x-ray analysis.

The late stage of HIV replication requires a virus-encoded aspartyl protease for maturational processing of structural proteins and replicative enzyme precursors. Inhibition of the protease results in immature, non-infectious virus particles and cessation of virus propagation.

HIV Protease Inhibitors

To date, numerous compounds that inhibit HIV protease function have been identified. The following table shows a variety of HIV protease inhibitors currently in various stages of clinical testing, and the companies exploring these compounds in HIV treatment.

| HIV Protease Inhibitors (I) | | |
|---|---|---|
| Compound | Drug Class | Company |
| Ro 31-8959 | Hydroxyethylamine | Hoffman-LaRoche |
| MK-639 | Hydroxyaminopentane amide | Merck, Sharpe & Dohme |
| ABT-538 | Symmetry-Based | Abbott |
| SC-52151 | Hydroxyethylurea | Searle/Monsanto |
| XM-323 | Cyclic Urea | Dupont/Merck |
| KNI-272 | Phenylnorstatine | Kyoto Pharm./NCI |
| U-103,017 | Pyranone | Upjohn/Pharmacia |
| AG-1343 | Hydroxyethylamine | Agouron |
| VX-478 | Hydroxyethylsulfonamide | Vertex/Glaxo-Wellcome |
| DPM-450 | Cyclic Urea | Dupont-Merck |
| BMS-182,193 | Aminoalcohol | Bristol-Myers |
| CGP-53820 | Pseudosymmetric Inhibitors | Squibb Ciba-Geigy |
| CGP-53437 | Hydroxyethylene Isosteres | Ciba-Geigy |
| HOE/BAY-793 | C2-Symmetric Peptidomimetic | Hoechst/Bayer |
| RPI-312 | Synthetic Peptide | Takeda Chemical Industries |

Structures are provided below for a selection of the above protease inhibitors.

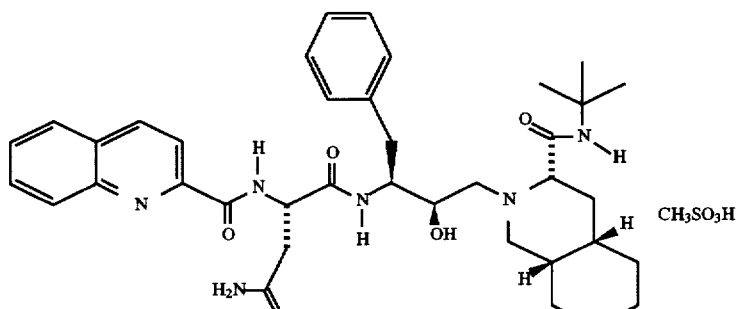

Ro 31-8959

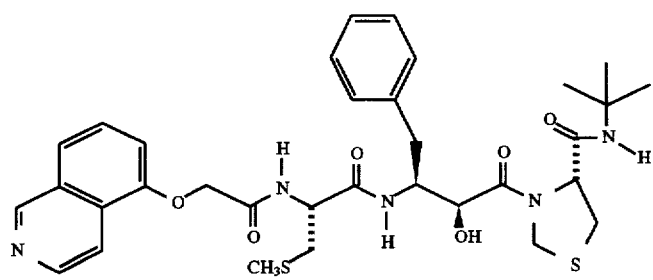

KNI-272

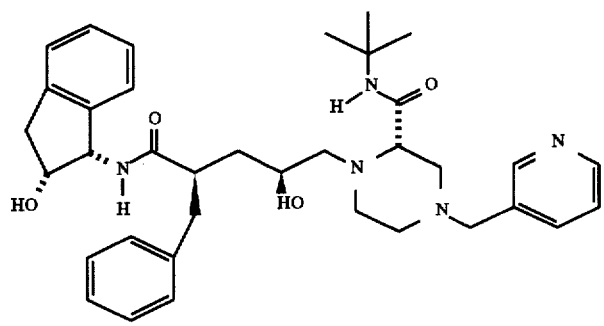

MK-639

-continued

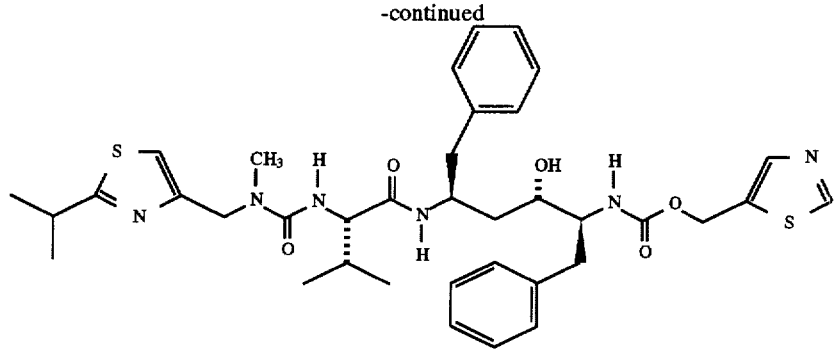

ABT-538

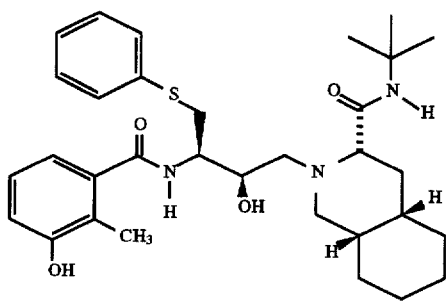

AG-1343

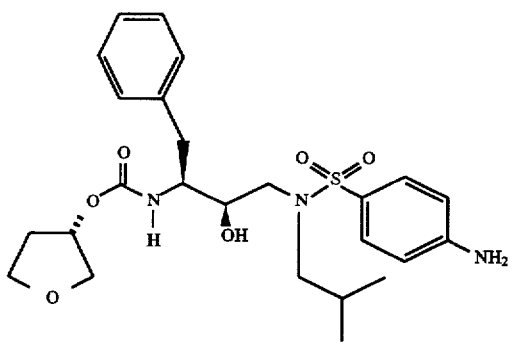

VX-478

These compounds make up one particularly promising new class of antiretrovirals because they attack HIV at late stages of its replication cycle, and thus are potentially active against viruses harbored in chronically infected cells. By contrast, currently licensed anti-HIV drugs, such as AZT, ddI, ddC, and more recently d4T, work as inhibitors of reverse transcriptase, a viral enzyme acting at early stages of HIV replication. While these drugs can block HIV infection and thus protect cells that are not yet infected, they are essentially inactive against cells that are already infected, such as chronically infected cells. Once infection is established in the cells (i.e., HIV genetic material is integrated into the host cell genome), reverse transcriptase is no longer required for viral replication. However, protease enzyme is essential for virions to produce infectious, mature virus particles. The function of HIV protease inhibitors is to render newly produced virus particles noninfectious. Therefore, drugs active in chronically infected cells are urgently needed, to be used either alone or in combination with other anti-HIV drugs, to improve the chances of success in therapy for HIV infection.

One factor that could affect the relationship between the in vitro $EC_{50}$ (median effective concentration) of a drug such as a protease inhibitor and the antiviral concentration of that drug required under physiological conditions in vivo is the extent and effect of protein binding. The antiviral activity of several HIV protease inhibitors has been shown to decrease in the presence of higher concentrations of human serum or plasma (Bilello, Abstract #419 1st Intl. Conference on Human Retroviruses, Dec. 12–16, 1993 Washington, D.C.; Bilello, Abstract I78, 34th Interscience Conference on Antimicrobial Agents and Chemotherapy Oct. 4–7, 1994). The higher binding affinity of HIV protease inhibitors is probably related to their lipophilicity (Kagavama et al, Antimicro. Agents and Chemother., 38:1107–1111, 1994). Sommadossi et al (Abstract "A Human Serum Glycoprotein Profoundly Affects Antiviral Activity of the Protease Inhibitor SC-52151 by Decreasing Its Cellular Uptake" The Second Nat'l Conference on Human Retroviruses and Related Infections, Washington, D.C., Jan. 30, 1995) and Bilello, et al (1993 supra) have recently shown that human alpha-1-acid glycoprotein (AAG) but not albumin, both major components of human plasma, can markedly reduce the antiviral activity of the protease inhibitors A77003 and SC-52151 and their analogs. AAG is an acute-phase protein with normal physiological levels of 0.5 to 1.5 mg/ml, which can increase after disturbance of homeostatis by infections, cancer, inflammation and injuries. The average value of AAG has been reported to be 50–100% higher in AIDS and cancer patients, as compared to healthy persons (Oei et al *J. AIDS*, 6:25–27, 1993).

The antiviral activity of certain experimental anti-HIV agents, including dextran sulfates, oligonucleotides and peptidomimetic-based protease inhibitors, and to a lesser extent, nucleoside analogs, (Kagavama et al (supra); Hartman et al *AIDS Res. Hum. Retroviruses*, 6:805–812, 1990) are markedly affected by high concentrations of human serum or components of human plasma. Although the structure of a particular drug candidate cannot be used to predict the in vitro plasma protein-binding affinity (Schmid in "The Plasma Proteins, Structure, Function and Genetic Control" Ed. by F. W. Putnam, Academic Press, Inc. New York, pp 184–228, 1975), the reduction in antiviral potency in the presence of physiologically relevant concentrations of plasma, or plasma components such as albumin or AAG, could be clinically important.

Another factor which affects the $EC_{50}$ and the antiviral concentration of protease inhibitors is the development of viral strains which are resistant to the protease inhibitors. Nearly every protease inhibitor and reverse transcriptase inhibitor used has the potential to result in resistant viral strains. This is especially the case in treatment of HIV infection, due to the ability of HIV to readily mutate and develop resistance. Mellors et al, (*International Antiviral News*, 3(1), pp 8–13, 1995) have recently reported on a variety of nucleoside RT inhibitors and protease inhibitors to which HIV has developed resistant mutations. (See also Condra et al *Nature* 374, pp. 569–571, 1995).

Thus, if therapy can be performed using less protease inhibitor while maintaining the same or even higher levels of antiviral activity, the tendency of the infectious agent being treated to mutate into a strain which is resistant to the protease inhibitor should be decreased.

In conclusion, binding of protease inhibitor to AAG leads to a major decrease in drug cellular uptake which results in alteration of anti-HIV activity. Therefore, sustained cellular uptake of protease inhibitors is critical for their in vivo anti-HIV activity, and for such cellular incorporation, the effect of AAG must be countered.

SUMMARY OF THE INVENTION

Accordingly one object of the present invention is to provide a method for increasing the cellular uptake and cellular concentration of protease inhibitors.

A further object of the present invention is to provide a method for increasing the cellular uptake and cellular concentration of one or more protease inhibitors in the presence of one or more additional therapeutic agents selected from reverse transcriptase inhibitors, antifusion/binding agents, anti-integrase agents and antiviral oligonucleotides.

A further object of the present invention is to provide a method for increasing the cellular uptake and cellular concentration of protease inhibitors for various pathogenic and infectious diseases including viral, fungal, antirenin, parasitic protozoan, cancer and antimicrobial diseases.

A further object of the present invention is to provide a method for improving the anti-HIV activity of HIV protease inhibitors.

A further object of the present invention is to provide a method to competitively bind AAG in the presence of a protease inhibitor.

A further object of the present invention is to provide a method to decrease the amount of protease inhibitor administered in protease inhibitor based therapy by increasing the availability of the protease inhibitor for cellular uptake.

These and other objects of the present invention have been satisfied by the discovery of potent AAG binders, such as antibiotics of the Macrolide and Lincosamide families, some of which bind AAG with a binding constant greater than the AAG protease inhibitor binding constant, thus increasing the cellular uptake of protease inhibitor, and the use of this discovery in a method for improving the cellular uptake and antiviral activity of therapeutic agents, such as protease inhibitors, especially the anti-HIV activity of protease inhibitors.

DETAILED DESCRIPTION OF THE PREFERRED EMBODIMENTS

The present invention relates to a method for improving the cellular uptake and antiviral activity of protease inhibitors, alone or in combination with one or more additional therapeutic agents, comprising administering, to a subject in need thereof, an effective amount of an AAG-binding compound having an affinity of AAG which is stronger than the affinity of AAG for the protease inhibitor.

In the present method, not all AAG binding compounds work experimentally. In fact, the AAG-binding compounds of the present invention must have a strong enough affinity for binding AAG to competitively bind the AAG in the presence of protease inhibitor.

Preferred AAG-binding compounds for use in the present invention include the Macrolide antibiotics and the Lincosamide antibiotics. More preferred Macrolide antibiotics include erythromycin, troleandomycin, clarithromycin and roxithromycin. Most preferred Macrolide antibiotics are clarithromycin and roxithromycin. A most preferred Lincosamide antibiotic is lincomycin.

In performing the method of the present invention, the AAG binding compound can be administered in any of the conventional methods for administering drug compositions. Such methods include, but are not limited to, intravenously, intraperitoneally, and orally. The compositions can be administered in the form of injectable solutions, ingestible solutions, tablets, capsules, lozenges, powders, etc. The preferred methods of administration are intravenously or orally. In the methods of the present invention, the AAG binding compounds can be given alone or as mixtures of two or more AAG binding compounds. Additionally, the AAG binding compound can be administered just prior to administration of a protease inhibitor, simultaneously with the administration of a protease inhibitor or after administration of the protease inhibitor, preferably prior to or simulaneously with administration of the protease inhibitor.

Any protease inhibitor used in protease inhibitor therapy may be used in the methods of the present invention. Protease inhibitors may be administered singly or as a mixture of two or more protease inhibitors. Preferred protease inhibitors include those listed in the Table on page 6 above, with SC-52151 being most preferred.

If the one or more protease inhibitors and one or more AAG binding compounds are being administered simultaneously they may be admixed immediately prior to administration or can be administered in any of the above mentioned forms for administration of the AAG binding compounds.

In a further embodiment of the present invention, one or more AAG binding compounds of the present invention may be administered in conjunction with administration of one or more protease inhibitors combined with one or more additional therapeutic agents selected from reverse transcriptase inhibitors, antifusion/binding agents, anti-integrase agents and antiviral oligonucleotides.

The AAG binding compounds of the present invention are used in a dosage range of from 0.1 times their normal dosage range in non-protease inhibitor based therapy up to their maximum tolerated dose (based on toxicity of the compounds). Preferably, the AAG binding compounds of the present invention are used in a dosage range of from 1 to 10 times their normal dosage in non-protease inhibitor based therapy. For example, roxithromycin is conventionally used in treatment of bacterial infections in an amount of 150 mg two times a day. However, in the method of the present invention, roxithromycin is administered in an amount ranging from 15 mg to 3000 mg twice a day.

By employing the present AAG binding compounds during protease inhibitor therapy, the present method provides for increased cellular uptake of the protease inhibitor. While the present inventors do not wish to be bound by any particular theory on the mode of action of the AAG binding compounds of the present invention, it is believed that the AAG binding compounds competitively bind the AAG in the presence of the protease inhibitor thus giving more free (unbound) protease inhibitor to be unbound to AAG. This is believed to provide more available protease inhibitor for cellular uptake.

The present method is useful in a variety of protease inhibitor based therapies, including, but not limited to, the treatment of various viral infections, such as those caused by retroviruses (e.g., HIV), hepadnoviruses (e.g., hepatitis C virus), herpesviruses (e.g., herpes simplex virus and cytomegalovirus) and myxoviruses (e.g., influenza virus), as well as parasitic protozoa (e.g., cryptosporidium and malaria), in cancer chemotherapy and pathological disorders which are treated using protease inhibitors.

By way of example, the effects of the present method on cellular uptake of an HIV protease inhibitor are described below.

SC-52151 is a member of a potent class of HIV protease inhibitors incorporating the (hydroxyethyl)urea isostere that shows a strong preference for the (R)-hydroxyl isomer in contrast to, for example, renin inhibitors where preference is for the (S)-hydroxyl configuration. The structure of SC-52151 is shown below as Formula I.

The HIV protease inhibitor SC-52151 is a tight-binding transition state analog containing a hydroxyethylurea isostere. In recent clinical trials, SC-52151 produced no measurable effect on markers of anti-HIV activity, including PCR RNA, P24 antigen or CD4+ counts, despite an oral absorption which leads to plasma levels five-to-eighty-fold above the in vitro $EC_{50}$. Human serum AAG has been shown to interfere with the virologic effects of various protease inhibitors. The following table shows the effect of AAG on the in vitro antiviral activity of protease inhibitors in HIV-infected CEM cells.

| Effect of human serum alpha-1 acid glycoprotein (AAG) on in vitro antiviral activity of protease inhibitors in HIV-infected CEM cells. | | | |
|---|---|---|---|
| | $EC_{90}$* (ng/ml) | | Fold Increase in $EC_{90}$ |
| Compound | AAG (0 mg/ml) | AAG (2 mg/ml) | Relative to Compound Alone |
| AZT | 9 | 10 | 0 |
| SC-52151 | 80 | 1970 | 24.6 |
| VX-478 | 40 | 1200 | 30 |
| Ro 31-8959 | 15 | 96 | 6.4 |
| MK-639 | 20 | 100 | 5.0 |

[1]$EC_{90}$ value was estimated from curve fit related to inhibition of reverse transcriptase activity associated with the clarified supernatants of HIV-infected cells.

Human serum AAG at physiological concentrations is seen to interfere with the in vitro anti-HIV activity of protease inhibitors with a 5 to 6-fold enhancement of the $EC_{90}$ value of Ro 31-8959 and MK-639 and a 25 fold increase in the $EC_{90}$ value of SC 52151. VX-478 and KNI-272 antiviral activity are also mostly affected by the presence of AAG. Protein binding studies revealed that SC-52151, VX-478 and KNI-272 were bound to AAG and to human plasma protein, respectively. Exposure of human HIV-infected PHA-activated peripheral blood mononuclear cells (PBMC) to 1 µM SC-52151 resulted in intracellular steady-state levels of 1.5 to 4.0 pmole/$10^6$ cells within 30 min, a 2–3 fold increase over uninfected cells. No difference in cellular content of SC-52151 was detected when cells were infected with either a low or high multiplicity of infection (MOI). Physiological concentrations of AAG, but not albumin, substantially affect the antiviral potency of SC-52151.

The AAG-binding compounds of the present invention provide increased activity of protease inhibitors, such as

I

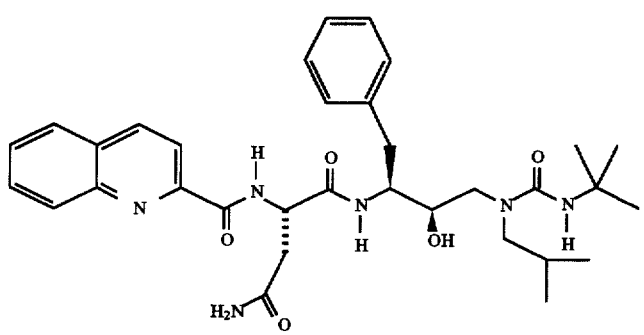

SC-52151 has similar in vitro antiviral potency, and selectivity as compared to other HIV protease inhibitors (Chang, *J. Physicians Assoc. Aids Res.*, July pp. 8–18, 1994).

SC-52151, by binding the AAG present, freeing up the protease inhibitors, or by preventing binding of protease inhibitor to AAG.

Having generally described this invention, a further understanding can be obtained by reference to certain specific examples which are provided herein for purposes of illustration only and are not intended to be limiting unless otherwise specified.

EXAMPLES

Preparation of SC-52151

Protease inhibitor SC-52151 was prepared using the method of Getman et al (*J. Med. Chem.*, 36:288–291 (1993)).

Effect of AAG-binding compounds on cellular uptake of SC-52151

The cellular accumulation of HIV protease inhibitor SC-52151 in phytohemagglutanin (PHA)-stimulated human peripheral blood mononuclear cells (PBMC) was measured after exposure to 1 µM of SC-52151 in the presence of 1 mg/ml of AAG and a modulating agent including AAG-binding compounds of the present invention at various concentrations. Each of the modulating agents was added 15 minutes before the addition of AAG and SC-52151 and the experiments were performed for 2 hours prior to measurement. All of the following experiments used human AAG. Similar results can be obtained using bovine AAG, although the activity and effect on cellular uptake of the present AAG binding compounds is attenuated using bovine AAG. The results are provided in the tables below.

TABLE 1

| Modulating Agent (µM) | Human AAG (1 mg/ml) | Cellular Uptake (pmole/$10^6$ cells*) | Percent of Control (%) |
| --- | --- | --- | --- |
| None | – | 1.44 | 100 |
| None | + | 0.12 | 8.3 |
| Erythromycin (50) | + | 0.55 | 38.2 |
| Erythromycin (100) | + | 0.85 | 59.0 |
| Erythromycin (500) | + | 1.50 | 104.2 |
| Troleandomycin (50) | + | 0.42 | 29.2 |
| Troleandomycin (100) | + | 0.64 | 44.4 |
| Troleandomycin (500) | + | 1.29 | 89.6 |

*1 pmole/$10^6$ cells = approx. 1 µM

Table 1 shows the effect of erythromycin and troleandomycin on cellular uptake of HIV protease inhibitor SC-52151 in the presence of AAG, compared to administration of SC-52151 in the absence of AAG and administration of HIV protease inhibitor SC-52151 in the presence of 1 mg/ml of AAG. As shown in the table, throughout the range of 50 µM to 500 µM the cellular concentration of the protease inhibitor markedly increases to essentially 100% of the level obtained in the absence of AAG. Even at low levels of erythromycin and troleandomycin of 50 µM the cellular concentration is at 30–40% of the control with no AAG, compared to the control experiment performed in the presence of AAG which gave reduced cellular concentration to only 8.3% of that obtained in the absence of AAG. Thus, it is clearly shown that macrolide antibiotics such as erythromycin and troleandomycin can significantly increase the cellular concentration of protease inhibitors.

Clarithromycin provides an even stronger effect on protease inhibitor cellular concentration than found with erythromycin or troleandomycin, as shown by the increase in cellular concentration of the protease inhibitor at lower doses of clarithromycin as compared to erythromycin or troleandomycin. This is shown in the results in Table 2.

TABLE 2

| Modulating Agent (µM) | Human AAG (1 mg/ml) | Cellular Uptake (pmole/$10^6$ cells*) | Percent of Control (%) |
| --- | --- | --- | --- |
| None | – | 1.02 | 100 |
| None | + | 0.09 | 8.8 |
| Clarithromycin (50) | + | 0.54 | 52.9 |
| None | – | 1.25 | 100 |
| None | + | 0.13 | 10.4 |
| Clarithromycin (100) | + | 1.02 | 82.0 |

*1 pmole/$10^6$ cells = approx. 1 µM

Not all AAG binding compounds are likely to be useful in the present invention at low concentrations. Further, not all macrolide antibiotics are useful, as shown below in Table 3 which provides the results obtained using midecamycin, oleandomycin and spiramycin. While some improvement in cellular concentration of the HIV protease inhibitor is obtained using these macrolide antibiotics, the effects are clearly inferior to the macrolide antibiotics having stronger binding affinities for AAG.

TABLE 3

| Modulating Agent (µM) | Human AAG (1 mg/ml) | Cellular Uptake (pmole/$10^6$ cells*) | Percent of Control (%) |
| --- | --- | --- | --- |
| Midecamycin (100) | + | 0.24 | 19.3 |
| Oleandomycin (100) | + | 0.29 | 23.3 |
| Spiramycin (100) | + | 0.23 | 18.5 |
| Azithromycin (100) | + | 0.18 | 17.7 |
| Josamycin (100) | + | 0.37 | 26.4 |
| Rokitamycin (100) | + | 0.34 | 24.3 |

*1 pmole/$10^6$ cells = approx. 1 µM

One of the strongest macrolide antibiotics for use in the present invention is roxithromycin. Tables 4 and 5 show the results obtained from two independent experiments using roxithromycin. It is interesting to note that the cellular concentration of the HIV protease inhibitor SC-52151 is not only improved compared to experiments performed in the presence of AAG and absence of roxithromycin, but the cellular concentration of SC-52151 is increased compared to controls performed in the absence of AAG, with the improvement in cellular concentration being as high as a 72.4% increase over the control. Accordingly, roxithromycin enhances the cellular concentration of protease inhibitors above and beyond the extent previously attainable when AAG is absent. As is evident from these results, the AAG binding ability of the macrolide antibiotic is not the only factor affecting the cellular concentration of the protease inhibitor since compounds having known potent AAG binding capability, such as midecamycin, even at 100 µM, did not markedly influence the cellular uptake of the protease inhibitor.

TABLE 4

| Modulating Agent (µM) | Human AAG (1 mg/ml) | Cellular Uptake (pmole/$10^6$ cells*) | Percent of Control (%) |
| --- | --- | --- | --- |
| None | – | 1.27 | 100 |
| None | + | 0.11 | 8.7 |
| Roxithromycin (10) | + | 0.27 | 21.6 |
| Roxithromycin (50) | + | 2.08 | 163.8 |
| Roxithromycin (100) | + | 2.19 | 172.6 |

*1 pmole/$10^6$ cells = approx. 1 µM

TABLE 5

| Modulating Agent (μM) | Human AAG (1 mg/ml) | Cellular Uptake (pmole/10⁶ cells*) | Percent of Control (%) |
|---|---|---|---|
| None | − | 1.47 | 100 |
| None | + | 0.10 | 6.8 |
| Roxithromycin (10) | + | 0.30 | 20.4 |
| Roxithromycin (20) | + | 0.97 | 66.0 |
| Roxithromycin (30) | + | 1.33 | 90.5 |
| Roxithromycin (40) | + | 1.96 | 133.3 |
| Roxithromycin (50) | + | 2.16 | 147.0 |

*1 pmole/10⁶ cells = approx. 1 μM

Table 6 shows the improvements in cellular concentration obtained using the Lincosamide antibiotic of lincomycin, compared to another Lincosamide antibiotic, clindamycin, which is known to bind AAG. The results again show that AAG binding is not the only factor at play in increasing cellular uptake of the protease inhibitor, since clindamycin shows negligible increase in protease inhibitor cellular uptake.

TABLE 6

| Modulating Agent (μM) | Human AAG (1 mg/ml) | Cellular Uptake (pmole/10⁶ cells*) | Percent of Control (%) |
|---|---|---|---|
| None | − | 1.44 | 100 |
| None | + | 0.12 | 8.3 |
| Lincomycin (50) | + | 0.43 | 29.9 |
| Lincomycin (100) | + | 0.55 | 38.2 |
| Lincomycin (500) | + | 1.28 | 88.8 |
| Clindamycin (100) | + | 0.15 | 10.4 |

*1 pmole/10⁶ cells = approx. 1 μM

The present invention requires the use of AAG binding compounds which have sufficient binding affinity with AAG to disrupt or prevent the AAG-protease inhibitor binding and increase the cellular uptake of the protease inhibitor. Table 7 shows that not all AAG binding compounds are useful in the present invention. The compounds of Table 7 are known to bind AAG (Kremer et al, Pharm. Rev. 40(1), 1–47, 1988 and references cited therein). However, even though these compounds are known to bind AAG, they do not appear to have a significant effect on protease inhibitor concentration at clinically relevant concentration, with the exception of verapamil, which shows a moderate improvement in SC-52151 cellular uptake.

TABLE 7

| Modulating Agent (μM) | Human AAG (1 mg/ml) | Cellular Uptake (pmole/10⁶ cells*) | Percent of Control (%) |
|---|---|---|---|
| None | − | 1.44 | 100 |
| None | + | 0.12 | 8.3 |
| Thioridazine (5) | + | 0.17 | 11.8 |
| None | − | 0.65 | 100 |
| None | + | 0.06 | 9.2 |
| Verapamil (10) | + | 0.23 | 35.4 |
| None | − | 0.58 | 100 |
| None | + | 0.074 | 12.6 |
| Prazocin (5) | + | 0.089 | 15.2 |
| Disopyramide (5) | + | 0.11 | 19.3 |
| Dipyridamole (1) | + | 0.084 | 14.3 |
| Indomethacin (5) | + | 0.083 | 14.2 |
| Oxprenolol (5) | + | 0.10 | 17.7 |

*1 pmole/10⁶ cells = approx. 1 μM

The increased cellular uptake of protease inhibitor exhibited in the above studies prompted further investigation into whether the antiviral activity of protease inhibitors would be restored in the presence of macrolide antibiotics which were shown to increase cellular uptake of the antiviral compound.

Antiviral studies

Cells.

Human PBMC from healthy HIV-1 seronegative and hepatitis B virus seronegative donors were isolated by Ficoll-Hypaque discontinuous gradient centrifugation at 1,000×g for 30 minutes, washed twice in phosphate-buffered saline (pH 7.2; PBS), and pelleted at 300×g for 10 minutes. Before infection, the cells were stimulated by phytohemagglutanin (PHA) at a concentration of 8 μg/ml for three days in RPMI 1640 medium supplemented with 15% heat-inactivated fetal calf serum, 1.5 mM L-glutamine, penicillin (100 U/ml), streptomycin (100 μg/ml), and 4 mM sodium bicarbonate buffer.

Viruses.

HIV-1 (strain LAV-1) was obtained from the CDC, Atlanta, Ga. The virus was propagated in human PBMC using RPMI 1640 medium, as described previously (McDougal et al. *J. Immun. Meth.* 76:171–183, 1985) without PHA or fungizone and supplemented with 100 U/ml recombinant interleukin-2 (Cetus) and 7 μg/ml DEAE-dextran (Pharmacia, Uppsala, Sweden). Virus obtained from cell-free culture supernatant was titrated and stored in aliquots at −700° C. until use.

Inhibition of virus replication in human PBMC.

Uninfected PHA-stimulated human PBMC were uniformly distributed among 25 cm² flasks to give a 5 ml suspension containing about 2×10⁶ cells/ml. Suitable dilutions of virus were added to infect the cultures. The mean reverse transcriptase (RT) activity of the inocula was 60,000 dpm RT activity/10⁶ cells (MOI=0.01). The drugs at twice their final concentrations in 5 ml of RPMI 1640 medium, supplemented as described above, were added to the cultures. Uninfected and untreated PBMC at equivalent cell densities were grown in parallel as controls. The cultures were maintained in a humidified 5% $CO_2$-95% air incubator at 37° C. for six days after infection at which point all cultures were sampled for supernatant RT activity. Previous studies had indicated that maximum RT levels were obtained at that time. Concentrations which provided a 90% decrease in RT activity associated with cell supernatent as compared to untreated controls are reported below as $EC_{90}$ values.

RT activity assay.

Six ml supernatant from each culture was clarified from cells at 300×g for 10 minutes. Virus particles were pelleted from 5 ml samples at 40,000 rpm for 30 minutes using a Beckman 70.1 Ti rotor and suspended in 200 μl of virus disrupting buffer (50 mM Tris-HCl, pH 7.8, 800 mM NaCl, 20% glycerol, 0.5 mM phenylmethyl sulfonyl fluoride, and 0.5% Triton X-100).

The RT assay was performed in 96-well microtiter plates, as described by Spira et al (*J. Clin. Microbiol.* 25:97–99, 1987). The reaction mixture, which contained 50 mM Tris-HCl pH 7.8, 9 mM $MgCl_2$, 5 mM dithiothreitol, 4.7 μg/ml $(rA)_n \cdot (dT)_{12-18}$, 140 μM dATP, and 0.22 μM [³H]TTP (specific activity 78.0 Ci/mmol, equivalent to 17,300 cpm/pmol; NEN Research Products, Boston, Mass.), was added to each well. The sample (20 μl) was added to the reaction mixture which was then incubated at 37° C. for 2 hours. The reaction was terminated by the addition of 100 μl 10% trichloroacetic acid (TCA) containing 0.45 mM sodium pyrophosphate. The acid-insoluble nucleic acids which precipitated were collected on glass filters using a Skatron semi-automatic harvester (setting 9). The filters were washed with 5% TCA and 70% ethanol, dried, and placed in scintillation vials. Four ml of scintillation fluid (Ecolite, ICNm, Irvine, Calif.) were added and the amount of radioactivity in each sample was determined using a Packard Tri-Carb liquid scintillation analyzer (model 2,000CA). The results were expressed in dpm/ml of original clarified supernatant. The procedures for the anti-HIV-1 assays in PBMC described above have been published (see Schinazi. et al. in *Antimicrob. Agents Chemother.* 32:1784–1789, 1988 and Schinazi, et al. in *Antimicrob. Agents Chemother.* 34:1061–1067 1990). The CEM studies were performed as described by Schinazi, et al. in *Antimicrob. Agents Chemother.* 36:2423–2431, 1992.

The following Table 8 provides the results of the antiviral studies on restoration of the anti-HIV activity of SC-52151 by Macrolide antibiotics in acutely infected PBM and CEM cells.

What is claimed as new and desired to be secured by Letters Patent of the United States is:

1. A method for improving cellular uptake of a protease inhibitor that binds alpha-1-acid glycoprotein during protease inhibitor-based therapy, comprising administering, to a subject in need thereof, an effective amount of one or more alpha-1-acid glycoprotein (AAG) binding compounds.

2. The method of claim 1, wherein said one or more AAG-binding compounds are selected from the group consisting of macrolide antibiotics and lincosamide antibiotics.

3. The method of claim 2, wherein said one or more AAG-binding compounds are macrolide antibiotics selected from the group consisting of erythromycin, troleandomycin, clarithromycin, and roxithromycin.

4. The method of claim 2, wherein said one or more AAG-binding compounds is lincomycin.

TABLE 8

Restoration of Anti-HIV Activity of SC-52151 by Macrolide Antibiotics in Acutely Infected Cells

| | Experiment in acutely infected human PBM cells | | | Experiment in infected CEM cells | |
| --- | --- | --- | --- | --- | --- |
| Treatment | $EC_{90}$ for drug alone or SC-52151 in combination | Units for drug alone or SC-52151 in combinatin | Fold decrease in EC90 relative to SC-52151 and AAG | $EC_{90}$, $\mu M$ for drug alone or SC-5251 in combination | Fold decrease in EC90 relative to SC-52151 and AAG |
| SC-52151 | 0.14 | $\mu M$ | | 0.14 | |
| AAG | >5 | mg/ml | | | |
| Clarithromycin | >600 | $\mu M$ | | | |
| Erythromycin | >1000 | $\mu g/ml$ | | 107.0 | |
| Roxithromycin | >1000 | $\mu M$ | | | |
| SC-52151 + AAG (1 mg/ml) | 1.22 | $\mu M$ | | 1.18 | |
| SC-52151 + AAG (1 mg/ml) + Clarithromycin (0.5 $\mu M$) | 0.63 | $\mu M$ | 1.9 | | |
| SC-52151 + AAG (1 mg/ml) + Clarithromycin (5 $\mu M$) | 0.26 | $\mu M$ | 4.7 | | |
| SC-52151 + AAG (1 mg/ml) + Clarithromycin (30 $\mu M$) | 0.062 | $\mu M$ | 19.7 | | |
| SC-52151 + AAG (1 mg/ml) + Clarithromycin (50 $\mu M$) | <0.01 | $\mu M$ | >122 | | |
| SC-52151 + AAG (1 mg/ml) + Erythromycin (10 $\mu g/ml$) | 0.58 | $\mu M$ | 2.1 | 0.59 | 2.0 |
| SC-52151 + AAG (1 mg/ml) + Erythromycin (50 $\mu g/ml$) | 0.14 | $\mu M$ | 8.7 | | |
| SC-52151 + AAG (1 mg/ml) + Erythromycin (100 $\mu g/ml$) | 0.033 | $\mu M$ | 37.0 | <0.01 | >118 |
| SC-52151 + AAG (1 mg/ml) + Roxithromycin (1 $\mu M$) | 0.97 | $\mu M$ | 1.3 | | |
| SC-52151 + AAG (1 mg/ml) + Roxithromycin (10 $\mu M$) | 0.53 | $\mu M$ | 2.3 | | |
| SC-52151 + AAG (1 mg/ml) + Roxithromycin (30 $\mu M$) | 0.059 | $\mu M$ | 20.7 | | |
| SC-52151 + AAG (1 mg/ml) + Roxithromycin (50 $\mu M$) | 0.05 | $\mu M$ | 24.4 | | |

From the above data, it is important to note that clarithromycin, erythromycin and roxithromycin are all essentially inactive with respect to antiviral activity against HIV-1 up to 600 µM. When only SC-52151 is present in the PBM or CEM cells, the $EC_{90}$ of SC-52151 is 0.14 µM. When AAG is added, the $EC_{90}$ of SC-52151 in PBM cells increases an order of magnitude to 1.22 µM (1.18 µM in CEM cells). However, when the AAG-binding compound of the present invention, namely clarithromycin, erythromycin and roxithromycin, are added there is a dose related decrease in $EC_{90}$, indicating greater antiviral potency. Specifically, the addition of the AAG-binding compounds of the present invention provides increased cellular uptake of SC-52151, which translates to increased antiviral activity. In fact, the AAG-binding compounds in the above table provide increases in antiviral activity beyond that achieved with SC-52151 alone. This enhanced activity is not cell line dependent, as confirmed by the above results in both PBM cells and CEM cells.

Obviously, additional modifications and variations of the present invention are possible in light of the above teachings. It is therefore to be understood that within the scope of the appended claims, the invention may be practiced otherwise than as specifically described herein.

5. The method of claim 1, wherein said one or more AAG-binding compounds are administered intravenously.

6. The method of claim 1, wherein said one or more AAG-binding compounds are administered orally.

7. The method of claim 1, wherein said one or more AAG-binding compounds are administered simultaneously with administration of said protease inhibitor.

8. The method of claim 1, wherein said one or more AAG-binding compounds are administered after administration of said protease inhibitor.

9. The method of claim 1, further comprising administering said protease inhibitor after administration of said one or more AAG-binding compounds.

10. The method of claim 1, wherein said one or more AAG-binding compounds are administered in an amount of from 0.1 times a normal dosage used in non-protease inhibitor based therapy up to a toxicological limit of said one or more AAG-binding compounds, from 1 to 3 times daily.

11. The method of claim 3, wherein said one or more AAG-binding compounds is roxithromycin or clarithromycin or a mixture thereof.

12. The method of claim 11, wherein said roxithromycin is administered in an amount of from 15 mg to 3000 mg, from 1 to 3 times daily.

13. A method for treatment of HIV infection, comprising administering, to a subject in need thereof, an HIV protease inhibitor that binds alpha-1 acid glycoprotein and one or more alpha-1-acid glycoprotein (AAG) binding compounds, wherein said one or more AAG-binding compounds is administered in an amount effective to increase cellular uptake of said HIV protease inhibitor when compared to cellular uptake of said HIV protease inhibitor in the absence of said one or more AAG-binding compounds.

14. The method of claim 13, wherein said one or more AAG-binding compounds are selected from the group consisting of macrolide antibiotics and lincosamide antibiotics.

15. The method of claim 14, wherein said one or more AAG-binding compounds are macrolide antibiotics selected from the group consisting of erythromycin, troleandomycin, clarithromycin, and roxithromycin.

16. The method of claim 15, wherein said one or more AAG binding compounds is roxithromycin or clarithromycin or a mixture thereof.

17. The method of claim 14, wherein said one or more AAG-binding compounds is lincomycin.

18. The method of claim 13, wherein said one or more AAG-binding compounds are administered simultaneously with administration of said HIV protease inhibitor.

19. The method of claim 13, wherein said one or more AAG-binding compounds are administered after administration of said HIV protease inhibitor.

20. The method of claim 13, wherein said HIV protease inhibitor is administered after administration of said one or more AAG-binding compounds.

21. A method for improving cellular uptake of a protease inhibitor, comprising administering, to a subject in need thereof, an effective amount of one or more alpha-1-acid glycoprotein (AAG)binding compounds along with the administration of one or more protease inhibitors that bind alpha-1-acid glycoprotein and one or more additional agents selected from the group consisting of reverse transcriptase inhibitors, antifusion/binding agents, anti-integrase agents, and antiviral oligonucleotides.

22. The method of claim 21, wherein said one or more AAG-binding compounds are selected from the group consisting of macrolide antibiotics and lincosamide antibiotics.

23. The method of claim 21, wherein said one or more AAG-binding compounds are macrolide antibiotics selected from the group consisting of erythromycin, troleandomycin, clarithromycin, and roxithromycin.

24. The method of claim 21, wherein said one or more AAG-binding compounds is lincomycin.

25. The method of claim 21, wherein said one or more AAG-binding compounds are administered intravenously.

26. The method of claim 21, wherein said one or more AAG-binding compounds are administered orally.

27. The method of claim 21, wherein said one or more AAG-binding compounds are administered simultaneously with administration of said one or more protease inhibitors and said one or more additional agents.

28. The method of claim 21, wherein said one or more AAG-binding compounds are administered after administration of said one or more protease inhibitors and said one or more agents.

29. The method of claim 21, wherein said one or more protease inhibitors and said one or more agents are administered after administration of said one or more AAG-binding compounds.

30. The method of claim 23, wherein said one or more AAG-binding compounds is roxithromycin or clarithromycin or a mixture thereof.

31. The method of claim 30, wherein said roxithromycin is administered in an amount of from 15 mg to 3000 mg, from 1 to 3 times daily.

32. A composition, comprising an effective therapeutic amount of one or more protease inhibitors that bind alpha-1-acid glycoprotein admixed with one or more alpha-1-acid glycoprotein (AAG)-binding compounds.

33. The composition of claim 32, further comprising one or more additional agents selected from the group consisting of reverse transcriptase inhibitors, antifusion/binding agents, anti-integrase agents, and antiviral oligonucleotides.

34. The composition of claim 32, wherein said one or more AAG-binding compounds are selected from the group consisting of macrolide antibiotics and lincosamide antibiotics.

35. The composition of claim 33, wherein said one or more AAG-binding compounds are macrolide antibiotics selected from the group consisting of erythromycin, troleandomycin, clarithromycin, and roxithromycin.

36. The composition of claim 33, wherein said one or more AAG-binding compounds is lincomycin.

37. The composition of claim 34, wherein said AAG-binding compound is roxithromycin or clarithromycin or a mixture thereof.

38. The composition of claim 32, wherein said protease inhibitor is a member selected from the group consisting of SC-52151, MK-639, ABT-538, Ro 31-8959, XM-323, KNI-272, U-103,017, AG-1343, VX-478, DPM-450, BMS-182, 193, CGP-53820, CGP-53437, HOE/BAY-793, and RPI-312.

39. The composition of claim 37, wherein said protease inhibitor is a member selected from the group consisting of SC-52151, MK-639, ABT-538, Ro 31-8959, XM-323, KNI-272, U-103,017, AG-1343, VX-478, DPM-450, BMS-182, 193, CGP-53820, CGP-53437, HOE/BAY-793, and RPI-312.

* * * * *